(12) United States Patent
Suzuma et al.

(10) Patent No.: US 9,291,599 B2
(45) Date of Patent: Mar. 22, 2016

(54) MAGNETIC TESTING METHOD AND APPARATUS

(75) Inventors: Toshiyuki Suzuma, Tokyo (JP); Yoshiyuki Nakao, Tokyo (JP); Makoto Sakamoto, Tokyo (JP); Yoshiyuki Oota, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 106 days.

(21) Appl. No.: 14/238,958

(22) PCT Filed: Aug. 15, 2012

(86) PCT No.: PCT/JP2012/070723
§ 371 (c)(1),
(2), (4) Date: Feb. 14, 2014

(87) PCT Pub. No.: WO2013/024858
PCT Pub. Date: Feb. 21, 2013

(65) Prior Publication Data
US 2014/0191751 A1    Jul. 10, 2014

(30) Foreign Application Priority Data
Aug. 18, 2011  (JP) ................... 2011-178915

(51) Int. Cl.
*G01N 27/82* (2006.01)
*G01N 27/83* (2006.01)
*G01N 27/90* (2006.01)

(52) U.S. Cl.
CPC ............... *G01N 27/82* (2013.01); *G01N 27/83* (2013.01); *G01N 27/902* (2013.01)

(58) Field of Classification Search
CPC ............................ G01N 27/902; G01N 27/82
USPC ................................ 324/232, 220, 240, 242
See application file for complete search history.

(56) References Cited

U.S. PATENT DOCUMENTS

| | | | | |
|---|---|---|---|---|
| 4,602,212 A | * | 7/1986 | Hiroshima et al. | 324/227 |
| 5,491,409 A | * | 2/1996 | Flora et al. | 324/242 |
| 6,249,119 B1 | * | 6/2001 | Curtis et al. | 324/242 |
| 7,821,258 B2 | * | 10/2010 | Vinogradov | 324/240 |

FOREIGN PATENT DOCUMENTS

| | | |
|---|---|---|
| DE | 10 2008 020194 | 10/2009 |
| JP | 2-50676 | 4/1990 |
| JP | 7-253412 | 10/1995 |
| JP | 8-152424 | 6/1996 |
| JP | 8-304346 | 11/1996 |
| JP | 2001-41932 | 2/2001 |
| JP | 2008-128733 | 6/2008 |
| JP | 2011-002409 | 1/2011 |

* cited by examiner

*Primary Examiner* — Reena Aurora
(74) *Attorney, Agent, or Firm* — Clark & Brody

(57) ABSTRACT

A magnetic testing apparatus 100 according to the present invention comprises: a first magnetizing device 1 for applying a DC bias magnetic field to a test object P in substantially parallel to the direction in which a flaw F to be detected extends; a second magnetizing device 2 for applying an AC magnetic field to the test object P substantially perpendicularly to the direction in which the flaw F to be detected extends; and a detecting device 3 for detecting leakage flux produced by the magnetization of the test object P accomplished by the first magnetizing device 1 and the second magnetizing device 2.

2 Claims, 6 Drawing Sheets

Figure 2A
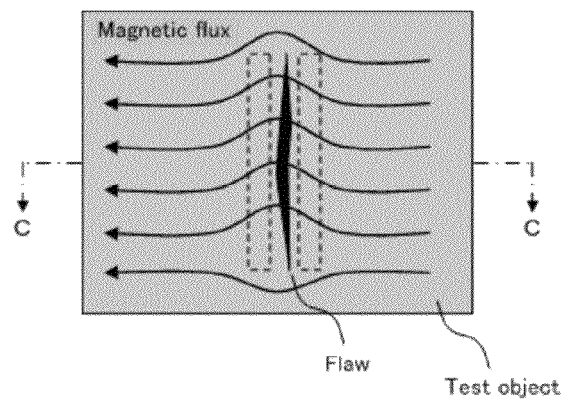
Figure 2B
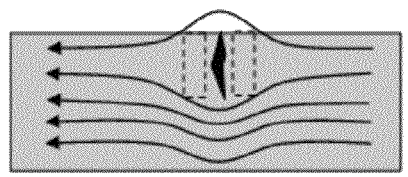
Figure 3B    Figure 3A
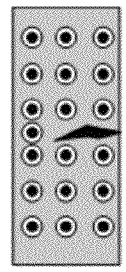 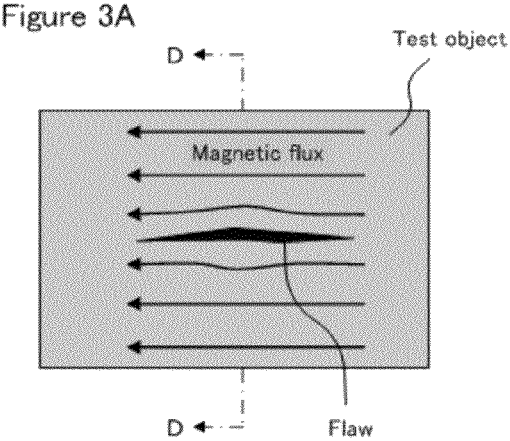

Figure 4A: Example 1(Axial flaw, Bias magnetic field is present)
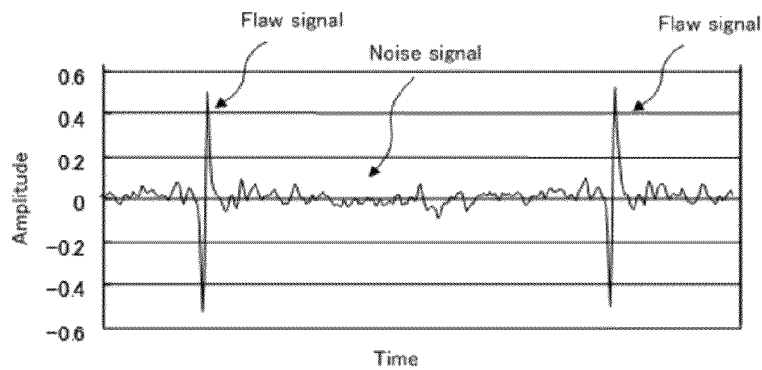
Figure 4B: Comparative example 1 (Axial flaw, Bias magnetic field is absent)
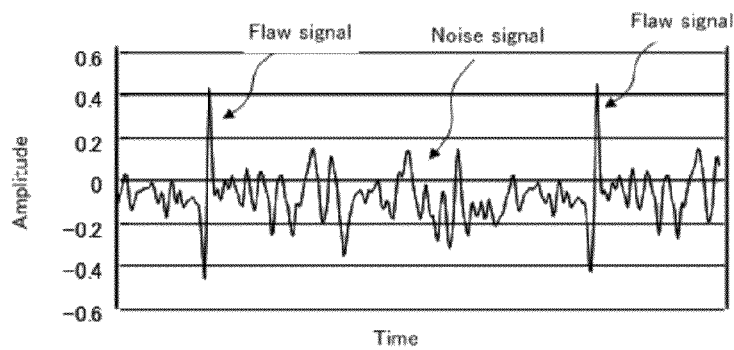
Figure 4C: Comparative example 2 (60 degrees-direction flaw, Bias magnetic field is present)
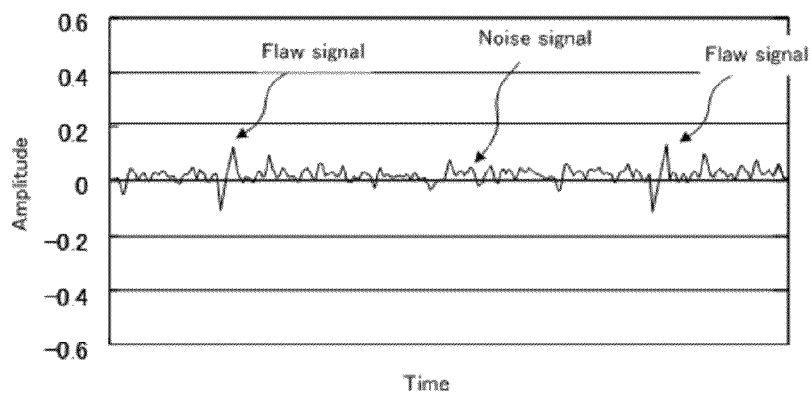

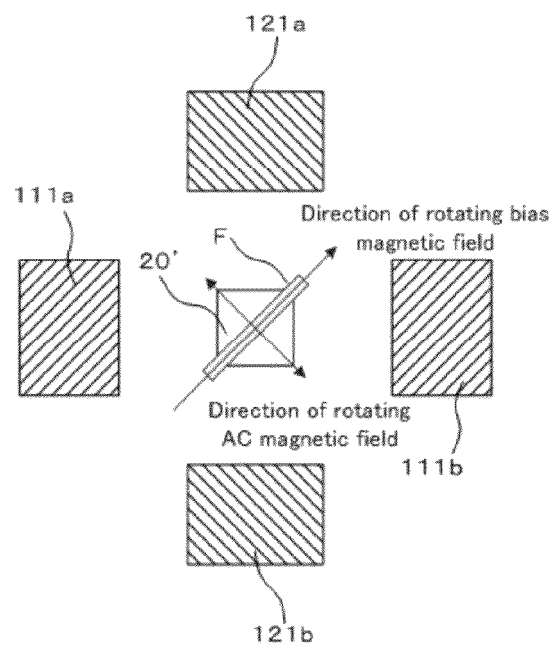

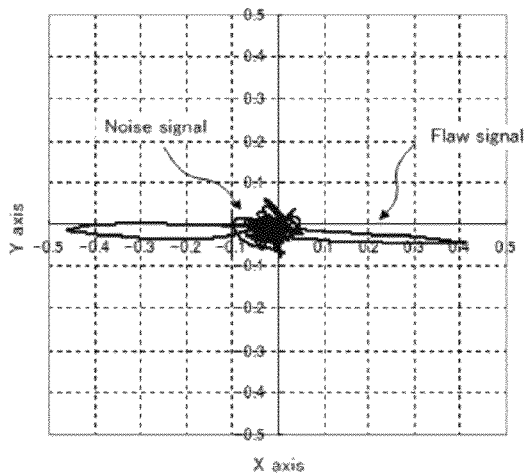
Figure 7A (Axial flaw)
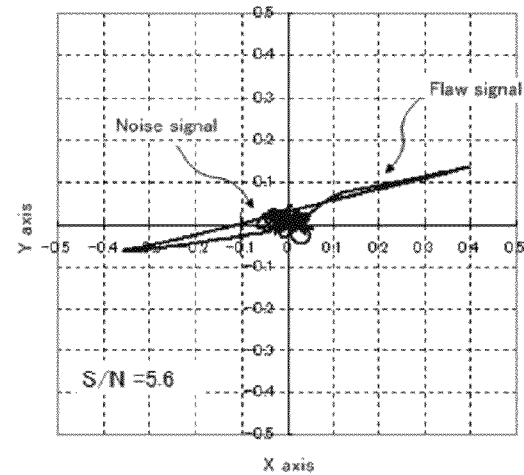
Figure 7B (15 degrees-direction flaw)
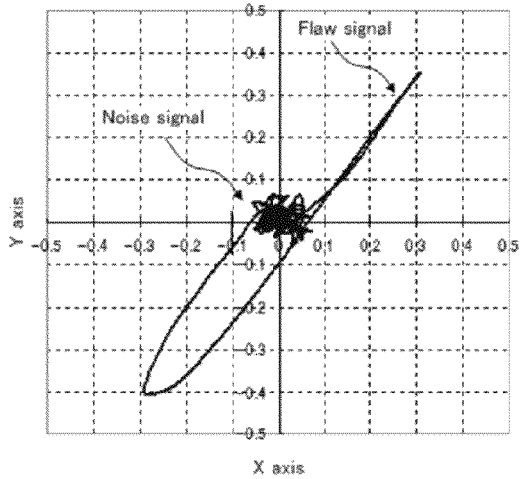
Figure 7C (45 degrees-direction flaw)
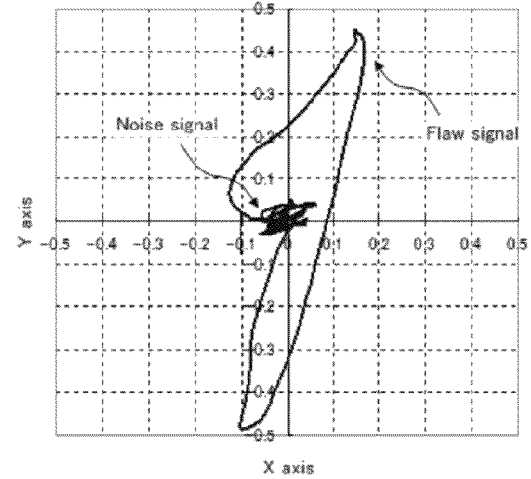
Figure 7D (75 degrees-direction flaw)

MAGNETIC TESTING METHOD AND APPARATUS

TECHNICAL FIELD

The present invention relates to a magnetic testing method and apparatus, which uses the fact that, when a test object consisting of a magnetic substance is magnetized by applying a magnetic field, the magnetic flux leaks to a surface space in a portion including a flaw, if any, which blocks a magnetic flux produced on the test object.

More particularly, the present invention relates to a magnetic testing method and apparatus, which can accurately detect a flaw by magnetizing a test object to such a degree that the object becomes magnetically saturated while solving a problem that a large magnetizing device is required when only a DC magnetic field is applied and a problem that the test object generates heat when only an AC magnetic field is applied.

BACKGROUND ART

Conventionally, as a method for nondestructively detecting a flaw that is present in a test object such as a steel plate and a steel pipe, a magnetic testing method (magnetic flux leakage testing method) has been known. This magnetic testing method is a flaw detecting method that uses the fact that, when a test object consisting of a magnetic substance is magnetized by applying a magnetic field, the magnetic flux leaks to a surface space in a portion including a flaw, if any, which blocks a magnetic flux produced on the test object.

In the above-described magnetic testing method, in order to increase the leakage flux leaking from the flaw to a detectable level, it is necessary to magnetize the test object to such a degree that the test object becomes magnetically saturated. Generally, as a magnetizing device for applying the magnetic field to the test object, an electromagnet, a coil, or the like of direct current or alternating current is used, and as a detecting device for detecting a leakage flux leaking from the flaw, a Hall element, a search coil, or the like is used.

As an apparatus for magnetically saturating the test object efficiently by using the magnetizing device such as an electromagnet, a coil, or the like, for example, the apparatuses described in Patent Literatures 1 and 2 have been proposed.

For the apparatus described in Patent Literature 1, a brush-form yoke is provided or a movable auxiliary yoke is provided between a magnetic pole (yoke open end) and a test object (material to be tested), whereby the occurrence of leakage flux caused by a gap between the magnetic pole and the test object is restrained, thereby improving the magnetization efficiency.

Unfortunately, for the apparatus described in Patent Literature 1, in the case where a DC electromagnet is used, the test object must be magnetically saturated in the whole thickness direction since the skin effect is not expected. In other words, there arises a problem that since a magnetic pole cross-sectional area larger than the cross-sectional area of the test object in the whole thickness direction is necessary, a large magnetizing device is required.

Hereunder, this apparatus is explained more specifically. The magnetic property of a ferromagnetic material constituting the test object such as a steel plate or a steel pipe has a nonlinear characteristic generally represented by a hysteresis curve. Therefore, magnetizing the test object up to about 1.4 T in terms of the magnetic flux density in the test object can be achieved by applying a relatively weak magnetic field. However, in order to obtain a magnetic flux density near the saturated magnetic flux density (1.7 to 1.81 T for a general carbon steel) necessary for sufficiently obtaining the leakage flux leaking from the flaw, it is necessary to apply an extremely strong magnetic field to the test object. Further, in DC magnetic saturation, the magnetic flux is distributed uniformly in the thickness direction of the test object. Therefore, in order to magnetically saturate the test object by using a DC electromagnet, it is necessary to use a large-size magnetizing device depending on the size (thickness) of the test object.

To solve the above-described problem, as described in Patent Literature 2, a magnetizing device using an AC electromagnet is adopted, and only the outer layer of test object has only to be magnetized by utilizing the skin effect. According to the apparatus described in Patent Literature 2, the size of the magnetizing device can be decreased. However, as described in Patent Literature 2, in the case where the test object is magnetized by applying an AC magnetic field to such a degree that the object becomes magnetically saturated, there arises a problem that since a large amount of heat is generated by an eddy current produced in the test object, an adverse influence such as decreased sensitivity or decreased service life of detecting device for detecting leakage flux occurs.

Hereunder, this apparatus is explained more specifically. In the case where the AC magnetic field is applied, since the magnetic flux can be concentrated on the outer layer of test object by the skin effect, this apparatus has an advantage that the size of the magnetizing device can be decreased as compared with the case where the DC magnetic field is applied. However, in order to suppress a noise signal caused by the material quality of test object, it is necessary to increase the magnetic flux density in the test object to the vicinity of the saturated magnetic flux density as in the case where the DC magnetic field is applied. In the case where the test object is magnetized by the AC magnetic field only to such a degree that the object becomes magnetically saturated, an electromotive force proportional to the time change of magnetic flux develops in the test object, which results in the occurrence of an eddy current. The current flowing in the test object is accompanied by resistance heat generation, and the test object becomes in an induction heated state, which causes the change in temperature of the leakage flux detecting device and its attachment jig provided in the surroundings. Generally, as the leakage flux detecting device, a sensor such as a Hall element, a search coil, or a flux gate is used. In the case where either of these sensors is used, an influence is exerted on the detection sensitivity of leakage flux and the service life on account of the change in temperature.

CITATION LIST

Patent Literature

[Patent Literature 1] JP8-152424A
[Patent Literature 2] JP2001-41932A

SUMMARY OF INVENTION

Technical Problem

The present invention has been made to solve the above-described problems with the prior art, and an objective thereof is to provide a magnetic testing method and apparatus, which can accurately detect a flaw by magnetizing a test object to such a degree that the object becomes magnetically saturated while solving a problem that a large magnetizing device is required when only a DC magnetic field is applied and a problem that the test object generates heat when only an AC magnetic field is applied.

Solution to Problem

To achieve the above objective, the present inventors conducted studies earnestly, and resultantly, paid attention to the fact that it is supposed that both of the problems of increased size of magnetizing device and heat generation of test object can be solved by magnetizing the test object by applying a DC magnetic field (bias magnetic field) in the range in which the magnetic flux density in the test object is liable to be relatively high (about 1.4 T) and further by magnetizing the test object by applying an AC magnetic field to detect the leakage flux leaking from a flaw by bringing the test object into a magnetically saturated state.

In the above-described attention, the objective of application of DC magnetic field is not to produce the leakage flux leaking from the flaw, but to increase the magnetic flux density of the whole of the test object including the vicinity of the flaw almost uniformly and to some degree. The present inventors found that in view of this objective, the application direction of DC magnetic field must be the direction in which the path of magnetic flux produced in the test object by the DC magnetic field is least liable to be blocked by the flaw (that is, the direction substantially parallel to the direction in which the flaw extends).

On the other hand, in the above-described attention, the objective of application of AC magnetic field is to produce the leakage flux leaking from the flaw. The present inventors found that in view of this objective, the application direction of AC magnetic field must be the direction in which the path of magnetic flux produced in the test object by the AC magnetic field is most liable to be blocked by the flaw (that is, the direction substantially perpendicular to the direction in which the flaw extends).

The present invention was completed by the above-described findings obtained by the present inventors.

A first invention of the present application provides a magnetic testing method comprising: applying a DC bias magnetic field to a test object in substantially parallel to the direction in which a flaw to be detected extends; applying an AC magnetic field to the test object substantially perpendicularly to the direction in which the flaw to be detected extends; and detecting the flaw to be detected based on leakage flux produced by the application of the magnetic fields.

According to the first invention of the present application, by applying the DC bias magnetic field in substantially parallel to the direction in which the flaw to be detected extends, in the range in which the magnetic flux density in the test object is liable to be relatively high, the test object can be magnetized almost uniformly in the state in which the path of magnetic flux is not blocked greatly by the flaw to be detected. According to this invention, in addition to the bias magnetic field, the AC magnetic field is applied. Thereby, the test object can be brought into the magnetically saturated state with relative ease. Also, since the direction of the applied AC magnetic field is substantially perpendicular to the direction in which the flaw to be detected extends, the leakage flux leaking from the flaw to be detected can be produced efficiently. As a result, the flaw to be detected can be detected with high accuracy.

Also, according to this invention, since the test object is magnetized by applying the DC bias magnetic field and the AC magnetic field combined with each other, it is advantageous that a large magnetizing device for magnetically saturating the test object is not required as compared with the case where the test object is magnetized by applying the DC magnetic field only.

Further, according to this invention, since the test object is magnetized by applying the DC bias magnetic field and the AC magnetic field combined with each other, it is also advantageous that even if the test object is magnetically saturated, the test object does not generate heat excessively as compared with the case where the test object is magnetized by applying the AC magnetic field only.

The above-described first invention of the present application is effective in the case where the direction in which the flaw to be detected extends is fixed and can be assumed beforehand. However, in the case where flaws extending in various directions are present in the test object, and flaws extending in any direction must be detected, the direction in which the DC bias magnetic field is applied (the direction substantially parallel to the direction in which the flaw extends) and the direction in which the AC magnetic field is applied (the direction substantially perpendicular to the direction in which the flaw extends) cannot made fixed. In order to be able to detect the flaw even if the flaw extends in any direction, it is effective to apply a rotating magnetic field, the direction of which changes moment by moment. When the rotating magnetic field is applied, the above-described findings obtained by the present inventors can also be taken advantage of to magnetize the test object up to the magnetically saturated state and to accurately detect the flaw while solving a problem that a large magnetizing device is required and a problem that the test object generates heat.

A second invention of the present application provides a magnetic testing method comprising: applying, to a test object, a rotating bias magnetic field which is excited by using an AC current as an exciting current; applying, to the test object, a rotating AC magnetic field which is excited by using a superimposed AC current in which a first AC current of the same frequency as that of the AC current that is the exciting current for the rotating bias magnetic field and a second AC current of a frequency higher than that of the first AC current are superimposed as an exciting current and which is 90 degrees out of phase with respect to the rotating bias magnetic field; and detecting a flaw based on leakage flux produced by the application of the magnetic fields.

According to the second invention of the present application the rotating bias magnetic field excited by using the AC current as the exciting current is applied to the test object. Although the AC current is used as the exciting current for exciting the rotating bias magnetic field, if the frequency thereof is made low (for example, about 10 Hz to 2 kHz), the AC current behaves in the same way as if the DC bias magnetic field in the first invention of the present application only changes the direction thereof moment by moment. Therefore, by the rotating bias magnetic field in the second invention of the present application as well, in the range in which the magnetic flux density in the test object is liable to be relatively high, the test object can be magnetized almost uniformly in the state in which the path of magnetic flux is not blocked greatly by the flaw (the flaw extending in substantially parallel to the direction at a certain moment of the rotating bias magnetic field).

According to this invention, in addition to the above-described rotating bias magnetic field, the rotating AC magnetic field that is 90 degrees out of phase with respect to the rotating bias magnetic field (that is, at a certain moment, the direction of rotating bias magnetic field and the direction of rotating AC magnetic field intersect at right angles with each other) is applied. This rotating AC magnetic field is excited by using the superimposed AC current in which the first AC current of the same frequency as that of the AC current that is the exciting current for the rotating bias magnetic field (if the frequency of the AC current that is the exciting current for the rotating bias magnetic field is low, the frequency of the first AC current is also low) and the second AC current of a frequency (for example, about 1 kHz to 500 kHz) higher than that of the first AC current are superimposed as an exciting current. Therefore, the AC magnetic field formed by the second AC current of high frequency is applied to the test object dominantly, whereas the first AC current of low frequency functions to rotate the direction of the formed AC magnetic field on the test object. This is because the induced electromotive force developing in the test object is proportional to the frequency of exciting current. In other words, the rotating AC magnetic field in the second invention of the present application behaves in the same way as if the above-described AC magnetic field in the first invention of the present invention only changes the direction thereof moment by moment.

In this invention, since in addition to the rotating bias magnetic field, the rotating AC magnetic field that is 90 degrees out of phase with respect to the rotating bias magnetic field is applied, the test object can be brought into the magnetically saturated state with relative ease. Also, since the direction of the applied rotating AC magnetic field is substantially perpendicular to the direction in which the flaw (the flaw extending in substantially parallel to the direction of the rotating bias magnetic field at a moment) extends, the leakage flux leaking from the flaw can be produced efficiently. As a result, the flaw can be detected accurately. In this invention, since the bias magnetic field is rotated, and also the AC magnetic field is rotated by shifting the phase thereof by 90 degrees with respect to the bias magnetic field, the flaws extending in various directions, which are present in the test object, can be detected.

Also, according to this invention, as in the first invention, it is advantageous that a large magnetizing device for magnetically saturating the test object is not required and that the test object does not generate heat excessively even in the magnetically saturated state.

The frequency of the first AC current has only to be set according to the relative travel speed of the magnetizing device for applying the rotating bias magnetic field and the rotating AC magnetic field with respect to the test object. Specifically, the frequency of the first AC current must be set so that the rotating bias magnetic field and the rotating AC magnetic field are rotated at least one turn during the time when the magnetizing device passes through the flaw. As the relative travel speed of the magnetizing device increases, the frequency of the first AC current must be set higher, and accordingly the frequency of the high-frequency second AC current must also be set higher. The ratio of the frequency of the first AC current to the frequency of the second AC current is preferably set at a ratio of a degree such that the second AC current can be synchronously detected as a reference signal (for example, 1:10 or higher).

To achieve the above objective, the present invention also provides a magnetic testing apparatus comprising: a first magnetizing device for applying a DC bias magnetic field to a test object in substantially parallel to the direction in which a flaw to be detected extends; a second magnetizing device for applying an AC magnetic field to the test object substantially perpendicularly to the direction in which the flaw to be detected extends; and a detecting device for detecting leakage flux produced by the magnetization of the test object accomplished by the first magnetizing device and the second magnetizing device.

To achieve the above objective, the present invention further provides a magnetic testing apparatus comprising: a first rotation magnetizing device for applying, to a test object, a rotating bias magnetic field which is excited by using an AC current as an exciting current; a second rotation magnetizing device for applying, to the test object, a rotating AC magnetic field which is excited by using an superimposed AC current in which a first AC current of the same frequency as that of the AC current that is the exciting current for the rotating bias magnetic field and a second AC current of a frequency higher than that of the first AC current are superimposed as an exciting current and which is 90 degrees out of phase with respect to the rotating bias magnetic field; and a detecting device for detecting leakage flux produced by the magnetization of the test object accomplished by the first rotation magnetizing device and the second rotation magnetizing device.

Advantageous Effect of Invention

The magnetic testing method and apparatus according to the present invention can accurately detect a flaw by magnetizing a test object to such a degree that the object becomes magnetically saturated while solving a problem that a large magnetizing device is required when only a DC magnetic field is applied and a problem that the test object generates heat when only an AC magnetic field is applied.

BRIEF DESCRIPTION OF DRAWINGS

FIGS. 2A and 2B (FIG. 2) are schematic views showing the state of the magnetic flux in the test object in the case where the direction of the DC magnetic field applied to the test object is substantially perpendicular to the direction in which the flaw extends.

FIGS. 3A and 3B (FIG. 3) are schematic views showing the state of the magnetic flux in the test object in the case where the direction of the DC magnetic field applied to the test object is substantially parallel to the direction in which the flaw extends.

FIGS. 4A, 4B and 4C (FIG. 4) are diagrams showing the test results of example 1 and comparative examples 1 and 2 of the present invention.

FIG. 6 is a schematic view showing the relationship between the magnetic fields formed by the magnetic testing apparatus as shown in FIGS. 5A, 5B, 5C and 5D.

FIGS. 7A, 7B, 7C and 7D (FIG. 7) are diagrams showing the test results of example 2 of the present invention.

DESCRIPTION OF EMBODIMENTS

Embodiments of the present invention will now be described by referring to the accompanying drawings as appropriate.

First Embodiment

In a magnetic testing apparatus in accordance with a first embodiment of the present invention, it is assumed that a test object is a pipe, and a flaw extending in the axial direction of pipe (hereinafter, referred to as an axial flaw) is to be detected.

Figure 1A:
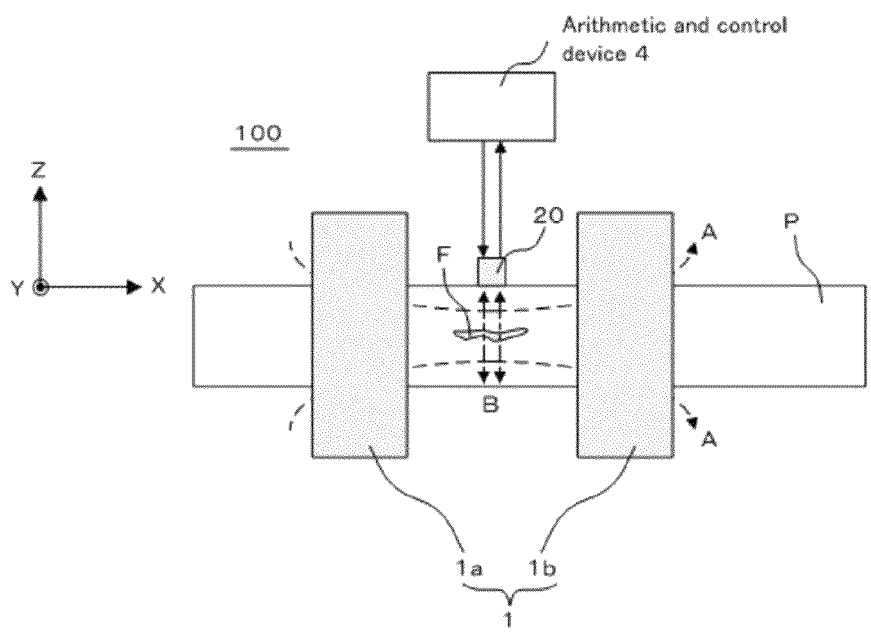
FIGS. 1A and 1B (FIG. 1) are views showing a general configuration of the magnetic testing apparatus in accordance with the first embodiment of the present invention.
Figure 1B:
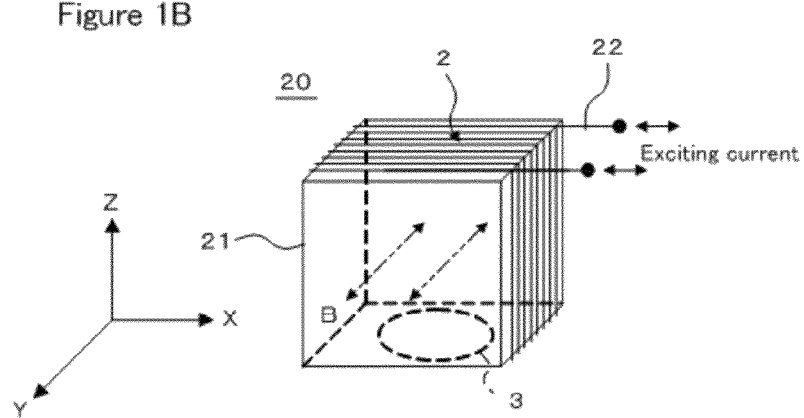

FIGS. 1A and 1B are views showing a general configuration of the magnetic testing apparatus in accordance with the first embodiment of the present invention. FIG. 1A is a general configuration view, and FIG. 1B is a schematic appearance view of a flaw detecting probe shown in FIG. 1A.

As shown in FIG. 1, a magnetic testing apparatus 100 in accordance with this embodiment includes a first magnetizing device 1 for applying a DC bias magnetic field to the pipe P in substantially parallel to the direction in which an axial flaw F, which is a flaw to be detected, extends (the axial direction of the pipe P (the X-direction shown in FIG. 1)), a second magnetizing device 2 for applying an AC magnetic field to the pipe P substantially perpendicularly to the direction in which the axial flaw F extends, and a detecting device 3 for detecting a leakage flux produced by the magnetization of the pipe P accomplished by the first magnetizing device 1 and the second magnetizing device 2. Also, the magnetic testing apparatus 100 in accordance with this embodiment includes an arithmetic and control device 4 for supplying an AC current to the second magnetizing device 2 and for detecting the axial flaw F by processing a flaw detection signal delivered from the detecting device 3.

The first magnetizing device 1 consists of a pair of encircling coils 1a and 1b through which the pipe P penetrates. Each of the pair of encircling coils 1a and 1b is supplied with a DC current, whereby a DC magnetic field (bias magnetic field) A is formed in the direction substantially parallel to the axial direction (X-direction) of the pipe P. That is, the direction of the bias magnetic field A is substantially parallel to the direction in which the axial flaw F extends.

The second magnetizing device 2 consists of an air-core type tangential coil. This tangential coil is formed by winding a conductor 22 in the axial direction (X-direction) of the pipe P around a core 21 consisting of a nonmagnetic substance. By supplying the AC current from the arithmetic and control device 4 to the conductor 22, an AC magnetic field B is formed in the direction substantially perpendicular to the axial direction (X-direction) of the pipe P (the Y-direction shown in FIG. 1). If the second magnetizing device 2 is arranged on the outer surface of the pipe P, the formed AC magnetic field B advances along the circumferential direction of the pipe P. That is, the direction of the AC magnetic field B is substantially perpendicular to the direction in which the axial flaw F extends.

The detecting device 3 is a planar coil for detecting the leakage flux in the Z-direction (refer to FIG. 1) intersecting at right angles with the X-direction and the Y-direction, which passes through the center of the second magnetizing device (tangential coil) 2. The detecting device 3 is attached to the lower surface of the core 21 that the second magnetizing device 2 has. The detecting device 3 detects the Z-direction leakage flux, and delivers it to the arithmetic and control device 4 as a flaw detection signal. The detecting device 3 is integrated with the second magnetizing device (tangential coil) 2 to form a flaw detecting probe 20.

The arithmetic and control device 4 supplies an AC current of a predetermined frequency to the second magnetizing device (tangential coil) 2. The arithmetic and control device 4 performs signal processing such as synchronous detection on the flaw detection signal delivered from the detecting device 3 with the AC current being the reference signal, and detects the axial flaw F.

According to the magnetic testing apparatus 100 having the above-described configuration, by applying the DC bias magnetic field A in substantially parallel to the direction in which the axial flaw F extends (X-direction), in the range in which the magnetic flux density in the pipe P is liable to be relatively high, the pipe P can be magnetized almost uniformly in the state in which the path of magnetic flux is not blocked greatly by the axial flaw F. Hereunder, this point is explained more specifically by referring to FIGS. 2 and 3 as appropriate.

FIGS. 2A and 2B are schematic views showing the state of the magnetic flux in the test object in the case where the direction of the DC magnetic field applied to the test object is substantially perpendicular to the direction in which the flaw extends. FIG. 2A is a plan view, and FIG. 2B is a sectional view taken in the direction of arrows C-C of FIG. 2A.

FIGS. 3A and 3B are schematic views showing the state of the magnetic flux in the test object in the case where the direction of the DC magnetic field applied to the test object is substantially parallel to the direction in which the flaw extends. FIG. 3A is a plan view, and FIG. 3B is a sectional view taken in the direction of arrows D-D of FIG. 3A.

As shown in FIG. 2, in the case where the direction of the DC magnetic field applied to the test object is substantially perpendicular to the direction in which the flaw extends, the magnetic flux produced by the application of DC magnetic field (indicated by solid-line arrow marks in FIG. 2) does not make a straight advance to a position just near the flaw and does not go around by changing the direction suddenly, but goes around while changing the direction gently with respect to the flaw. For this reason, around the flaw, regions in which the magnetic flux density is low, which are indicated by a broken line in FIG. 2, exist. Therefore, especially around the flaw, the DC magnetic field does not function as a bias magnetic field for increasing the leakage flux leaking from the flaw. In other words, in the case where DC magnetic saturation is effected so that the direction in which the flaw extends is substantially perpendicular to the direction of magnetic flux, the objective of DC magnetization such that the magnetic flux density in the test object is increased almost uniformly cannot be achieved.

On the other hand, a shown in FIG. 3, in the case where the direction of the DC magnetic field applied to the test object is substantially parallel to the direction in which the flaw extends, the magnetic flux produced by the application of DC magnetic field (indicated by solid-line arrow marks in FIG. 3) can go around a position close to the flaw in the state in which the path thereof is not blocked greatly by the flaw. For this reason, as shown in FIG. 3B, a region in which the magnetic flux is high exists up to the position close to the flaw, so that the objective of DC magnetization such that the magnetic flux density in the test object excluding the flaw is increased almost uniformly can be achieved.

For the reasons described above, in the magnetic testing apparatus 100 in accordance with this embodiment, the DC bias magnetic field A is applied in substantially parallel to the direction in which the axial flaw F extends (X-direction), and thereby the pipe P can be magnetized almost uniformly in the range in which the magnetic flux density in the pipe P is liable to be relatively high.

Also, in the magnetic testing apparatus 100 in accordance with this embodiment, in addition to the bias magnetic field A, the AC magnetic field B is applied. Thereby, the pipe P can be brought into the magnetically saturated state with relative ease. Also, since the direction of the applied AC magnetic field B is substantially perpendicular to the direction in which the axial flaw F extends, the leakage flux leaking from the axial flaw F can be produced efficiently. As a result, the axial flaw F can be detected with high accuracy.

Also, according to the magnetic testing apparatus 100 in accordance with this embodiment, since the pipe P is magnetized by applying the bias magnetic field A and the AC magnetic field B combined with each other, it is advantageous that a large magnetizing device for magnetically saturating the pipe P is not required as compared with the case where the pipe P is magnetized by applying the DC magnetic field only.

Further, according to the magnetic testing apparatus 100 in accordance with this embodiment, since the pipe P is magnetized by applying the bias magnetic field A and the AC magnetic field B combined with each other, it is also advantageous that even if the pipe P is magnetically saturated, the pipe P does not generate heat excessively as compared with the case where the pipe P is magnetized by applying the AC magnetic field only.

Hereunder, one example of a flaw detection test using the magnetic testing apparatus 100 in accordance with this embodiment is explained.

Example 1

In example 1, as the pipe P, which is a test object, a carbon steel pipe containing 0.25 mass % of carbon was used. On the surface of this pipe P, an artificial axial flaw having a depth of 0.5 mm and a length of 25 mm was provided. Also, as the encircling coils 1a and 1b, which are the first magnetizing device 1, coils each having 1000 turns, an outside diameter of 140 mm, an inside diameter of 80 mm, and a length (length along the axial direction of the pipe P) of 50 mm were used, and the encircling coils 1a and 1b were arranged at an interval of 40 mm in the axial direction of the pipe P. The current value of DC current supplied to each of the encircling coils 1a and 1b was made 1.5 A, and thereby a proper bias magnetic field (magnetic flux density in test object: about 1.5 T) was able to be applied. The current value of DC current necessary for magnetizing the pipe P to such a degree that leakage flux flaw detection can be made by this first magnetizing device 1 only (magnetic flux density in test object: about 1.8 T) is about 9 A. Therefore, according to this example, it can be seen that flaw detection can be carried out by a current value of about ⅙ as compared with the case where DC magnetic saturation is effected by the first magnetizing device 1 only.

Also, in this example, as the second magnetizing device (tangential coil) 2, a coil that was formed by winding the conductor 22 of 50 turns in the axial direction of the pipe P around the core 21, which consisted of a nonmagnetic cube one side of which was 6 mm, was used. The AC current supplied to the conductor 22 had a frequency of 50 kHz and a current value of 200 mA. A person skilled in the art can easily understand that this current value is very small as compared with the value of AC current energizing an electromagnet used for ordinary AC magnetic testing (magnetic testing made by application of AC magnetic field only). Also, it can be seen that if the second magnetizing device 2 of this example is used as a magnetizing device for forming an AC magnetic field, remarkably small size and light weight can be attained as compared with the conventional electromagnet. This offers a great advantage in the case where it is necessary to make flaw detection on the whole surface of test object by allowing the test object to make a straight advance and turning the magnetizing device for forming the AC magnetic field in the circumferential direction of test object. This is because the second magnetizing device 2 of this example can be used as a magnetizing device for forming the AC magnetic field to reduce the size of and to simplify the mechanism for turning the magnetizing device in the circumferential direction of test object.

Further, in this example, as the detecting device 3, a planar coil of 100 turns and 5 mm in diameter was used.

A flaw detection test was conducted under the above-described conditions.

Comparative Example 1

A flaw detection test was conducted under the same conditions as those of the example except that the bias magnetic field was not applied by the first magnetizing device 1.

Comparative Example 2

A flaw detection test was conducted under the same conditions as those of the example except that an artificial flaw (the depth and length were the same as those of example 1) extending in the direction inclining at 60 degrees with respect to the pipe axis direction was provided on the surface of the pipe P, and the orientation of the second magnetizing device 2 was adjusted so that the direction of the AC magnetic field formed by the second magnetizing device (tangential coil) 2 is substantially perpendicular to the direction in which the artificial flaw extends.

Evaluation Results

FIGS. 4A, 4B and 4C are diagrams showing the test results of example 1 and comparative examples 1 and 2. FIG. 4A shows the test result of example 1, FIG. 4B shows the test result of comparative example 1, and FIG. 4C shows the test result of comparative example 2. The waveforms shown in FIG. 4 are ones that were obtained by synchronously detecting the flaw detection signal delivered from the detecting device 3 with the AC current supplied to the second magnetizing device (tangential coil) 2 by the arithmetic and control device 4 being a reference signal.

As is apparent from the comparison of example 1 and comparative example 1 shown in FIG. 4, in comparative example 1 in which the bias magnetic field was not applied, the amplitude of flaw signal is somewhat small, and the amplitude of noise signal is large, whereas in example 1 in which the bias magnetic field was applied in substantially parallel to the direction in which the flaw extends, the amplitude of flaw signal increases, and inversely the amplitude of noise signal decreases. This result indicates that in the case where the bias magnetic field is applied in substantially parallel to the direction in which the flaw extends, the magnetic flux density of the whole of the pipe P including a portion close to the flaw increases, so that even if a magnetizing device in which the strength of the formed magnetic field is low, such as the air-core type tangential coil, is used, the pipe P becomes magnetically saturated easily. Therefore, this indicates that the leakage flux leaking from the flaw increases (therefore, the amplitude of flaw signal increases), and also noise signal caused by the magnetic nonuniformity of steel pipe material is suppressed.

Also, as is apparent from the comparison of comparative example 1 and comparative example 2 shown in FIG. 4, in comparative example 2 in which the bias magnetic field was applied, the amplitude of noise signal decreases as compared with comparative example 1 in which the bias magnetic field was not applied. However, as for the flaw signal, in comparative example 2 in which the bias magnetic field was applied, the amplitude thereof is inversely smaller. The reason for this is thought to be that since the direction of bias magnetic field is not parallel to the direction in which the flaw extends (makes an angle of 60 degrees), a region having a low magnetic flux density, which is produced by the going of the magnetic flux around the flaw, exists, which decreases the magnetic saturation level around the flaw, and hinders the production of leakage flux leaking from the flaw.

Second Embodiment

In a magnetic testing apparatus in accordance with a second embodiment of the present invention, the test object is a pipe, and flaws extending in various directions are to be detected.

Figure 5A:
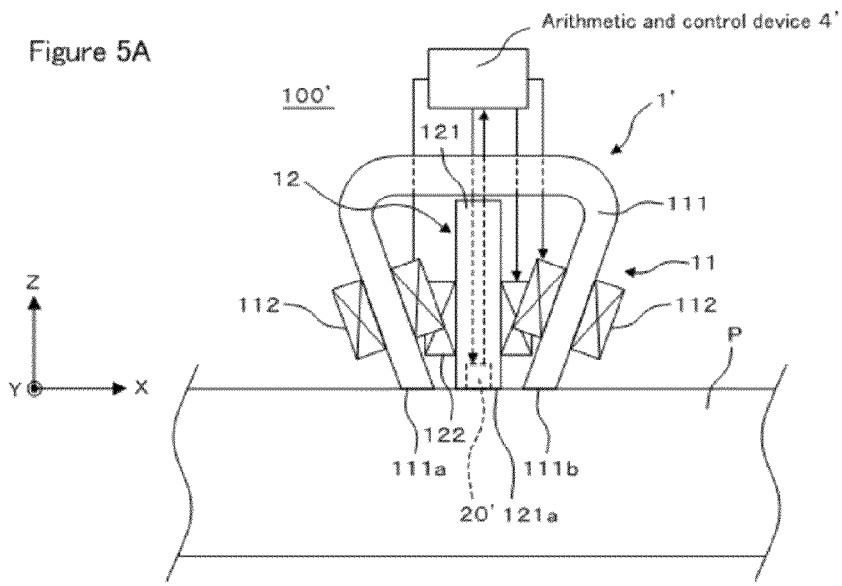
FIGS. 5A, 5B, 5C and 5D (FIG. 5) are views showing a general configuration of the magnetic testing apparatus in accordance with the second embodiment of the present invention.
Figure 5B:
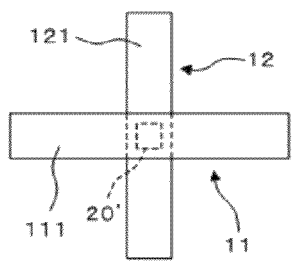
Figure 5C:
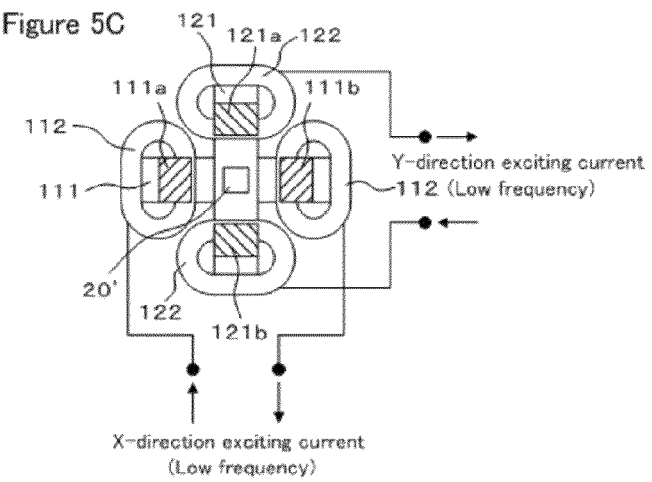
Figure 5D:
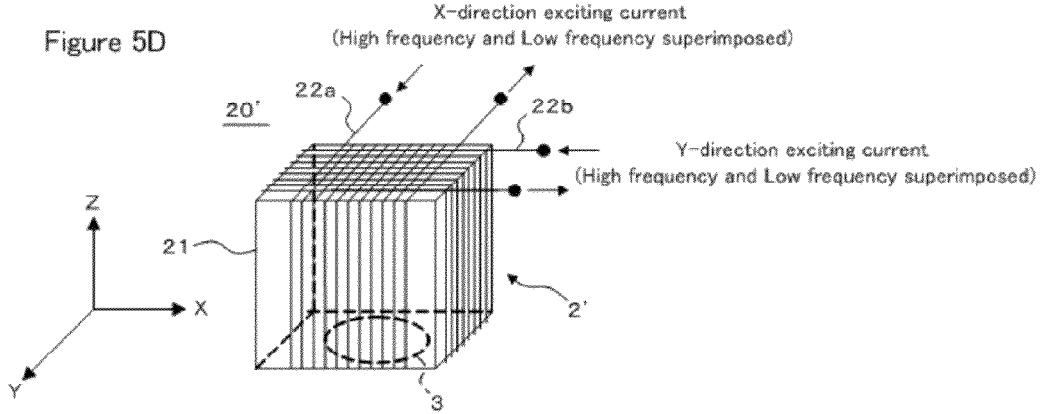

FIGS. 5A, 5B, 5C and 5D are views showing a general configuration of the magnetic testing apparatus in accordance with the second embodiment of the present invention. FIG. 5A is a front view showing the entire configuration, shown by being partially sectioned. FIG. 5B is a plan view. FIG. 5C is a back surface view. FIG. 5D is a schematic appearance view of a flaw detecting probe shown in FIGS. 5A to 5C. In FIG. 5B, the illustration of an exciting coil is omitted.

As shown in FIG. 5, a magnetic testing apparatus 100' in accordance with this embodiment includes a first rotation magnetizing device 1' for applying a rotating bias magnetic field to the pipe P, which is a test object, a second rotation magnetizing device 2' for applying a rotating AC magnetic field, which is 90 degrees out of phase with respect to the rotating bias magnetic field, to the pipe P, and the detecting device 3 for detecting a leakage flux produced by the magnetization of the pipe P accomplished by the first rotation magnetizing device 1' and the second rotation magnetizing device 2'. Also, the magnetic testing apparatus 100' in accordance with this embodiment includes an arithmetic and control device 4' for supplying an exciting current to the first rotation magnetizing device 1' and the second rotation magnetizing device 2' and for detecting the flaw by processing a flaw detection signal delivered from the detecting device 3.

The first rotation magnetizing device 1' is configured by a first electromagnet 11 and a second electromagnet 12 crossing the first electromagnet 11.

The first electromagnet 11 includes an inverse U-shaped yoke 111 and exiting coils 112, each of which is wound around each end portion of the yoke 111. By supplying an AC current from the arithmetic and control device 4' to the exciting coil 112, a magnetic field of the direction substantially parallel to the axial direction of the pipe P (X-direction shown in FIG. 5) is formed between magnetic poles 111a and 111b of the yoke 111.

The second electromagnet 12 includes an inverse U-shaped yoke 121 and exiting coils 122, each of which is wound around each end portion of the yoke 121. By supplying an AC current from the arithmetic and control device 4' to the exciting coil 122, a magnetic field of the direction (Y-direction shown in FIG. 5) substantially perpendicular to the axial direction of the pipe P (X-direction) is formed between magnetic poles 121a and 121b of the yoke 121.

By shifting the phase of the AC current (exciting current) supplied to the exciting coils 112 and 122 by 90 degrees, a synthetic magnetic field of the magnetic fields formed by the exciting coils 112 and 122 rotates through 360 degrees with the central position of the magnetic poles 111a, 111b, 121a and 121b being the center.

Thus, the first rotation magnetizing device 1' causes the rotating bias magnetic field to be applied to the pipe P.

The second rotation magnetizing device 2' has the same configuration as that of the exciting coil described in JP2008-128733, which was proposed by the present inventors. Specifically, like the second magnetizing device 2 of the first embodiment, the second rotation magnetizing device 2' consists of an air-core type tangential coil. However, for the second rotation magnetizing device 2', unlike the second magnetizing device 2, not only a conductor 22b is wound in the axial direction of the pipe P (X-direction) around the core 21 consisting of a nonmagnetic substance, but also a conductor 22a is also wound in the direction substantially perpendicular to the axial direction of the pipe P (Y-direction).

By supplying an exciting current (X-direction exciting current) from the arithmetic and control device 4' to the conductor 22a, an AC magnetic field of the direction substantially parallel to the axial direction of the pipe P (X-direction) is formed.

Also, by supplying an exciting current (Y-direction exciting current) from the arithmetic and control device 4' to the conductor 22b, an AC magnetic field of the direction (Y-direction) substantially perpendicular to the axial direction of the pipe P (X-direction) is formed.

By shifting the phases of the exciting currents supplied to the conductors 22a and 22b by 90 degrees from each other, a synthetic magnetic field of the AC magnetic fields formed by the conductors 22a and 22b rotates through 360 degrees with the central position of the second rotation magnetizing device 2' (tangential coil) being the center. That is, a rotating AC magnetic field is formed.

Specifically, to the second rotation magnetizing device 2', a superimposed AC current in which a first AC current of the same frequency as that of the AC current supplied to the first rotation magnetizing device 1' (supplied to the exciting coils 112 and 122) and a second AC current of a frequency higher than that of the first AC current are superimposed is supplied from the arithmetic and control device 4' as an exciting current. More specifically, to the conductor 22a of the second rotation magnetizing device 2', an X-direction exciting current in which the first AC current and the second AC current are superimposed is supplied.

On the other hand, to the conductor 22b of the second rotation magnetizing device 2', a Y-direction exciting current in which the first AC current and the second AC current are superimposed and the phase thereof is shifted by 90 degrees with respect to the X-direction exciting current is supplied.

The phases of the X-direction exciting current and the Y-direction exciting current are adjusted so that the rotating AC magnetic field formed by the second rotation magnetizing device 2' is 90 degrees out of phase with respect to the rotating bias magnetic field formed by the first rotation magnetizing device 1'.

Thus, the second rotation magnetizing device 1' causes the rotating AC magnetic field that is 90 degrees out of phase with respect to rotating bias magnetic field to be applied to the pipe P.

The detecting device 3 is, as in the first embodiment, a planar coil for detecting the leakage flux in the Z-direction (refer to FIG. 5) intersecting at right angles with the X-direction and the Y-direction, which passes through the center of the second rotation magnetizing device (tangential coil) 2'. The detecting device 3 is attached to the lower surface of the core 21 that the second rotation magnetizing device 2' has. The detecting device 3 detects the Z-direction leakage flux, and delivers it to the arithmetic and control device 4' as a flaw detection signal. The detecting device 3 is integrated with the second rotation magnetizing device (tangential coil) 2' to form a flaw detecting probe 20'.

The arithmetic and control device 4' supplies AC currents that are 90 degrees out of phase with respect to each other to the first electromagnet 11 and the second electromagnet 12 that the first rotation magnetizing device 1' has. Also, the arithmetic and control device 4' supplies superimposed AC currents (X-direction exciting current and Y-direction exciting current) in which the first AC current of the same frequency as that of the AC current supplied to the first rotation magnetizing device 1' and the second AC current of a frequency higher than that of the first AC current are superimposed and which are 90 degrees out of phase with respect to each other to the conductors 22a and 22b that the second rotation magnetizing device 2' has. The arithmetic and control device 4' adjusts the phases of the X-direction exciting current and the Y-direction exciting current, which are supplied to the second rotation magnetizing device 2', so that the rotating bias magnetic field formed by the first rotation magnetizing device 1' is 90 degrees out of phase with respect to the rotating AC magnetic field formed by the second rotation magnetizing device 2'.

Also, the arithmetic and control device 4' successively performs signal processing on the flaw detection signal delivered from the detecting device 3, the signal processing including synchronous detection in which the second AC current is used as a reference signal and synchronous detection in which the first AC current is used as a reference signal, to detect the axial flaw F.

FIG. 6 is a schematic view showing the relationship between the magnetic fields formed by the magnetic testing apparatus 100' having the above-described configuration.

According to the magnetic testing apparatus 100' in accordance with this embodiment, the rotating bias magnetic field excited by using an AC current as an exciting current is applied. Although the AC current is used as the exciting current for exciting the rotating bias magnetic field, if the frequency thereof is made low, the AC current behaves in the same way as if the above-described DC bias magnetic field formed by the magnetic testing apparatus 100 in accordance with the first embodiment only changes the direction thereof moment by moment. Therefore, by the rotating bias magnetic field formed by the magnetic testing apparatus 100' in accordance with the second embodiment as well, in the range in which the magnetic flux density in the pipe P is liable to be relatively high, the pipe P can be magnetized almost uniformly in the state in which the path of magnetic flux is not blocked greatly by the flaw (the flaw extending in substantially parallel to the direction at a certain moment of the rotating bias magnetic field) F.

According to the magnetic testing apparatus 100' in accordance with this embodiment, in addition to the rotating bias magnetic field, the rotating AC magnetic field that is 90 degrees out of phase with respect to the rotating bias magnetic field (that is, at a certain moment, the direction of rotating bias magnetic field and the direction of rotating AC magnetic field intersect at right angles with each other) is applied. This rotating AC magnetic field behaves in the same way as if the AC magnetic field described in the first embodiment only changes the direction thereof moment by moment.

In the magnetic testing apparatus 100' in accordance with this embodiment, since in addition to the rotating bias magnetic field, the rotating AC magnetic field that is 90 degrees out of phase with respect to the rotating bias magnetic field is applied, the pipe P can be brought into a magnetically saturated state with relative ease. Also, since the direction of the applied rotating AC magnetic field is substantially perpendicular to the direction in which the flaw (the flaw extending in substantially parallel to the direction of the rotating bias magnetic field at a moment) F extends, the leakage flux leaking from the flaw F can be produced efficiently. As a result, the flaw F can be detected accurately. In the magnetic testing apparatus 100' in accordance with this embodiment, since the bias magnetic field is rotated, and also the AC magnetic field is rotated by shifting the phase thereof by 90 degrees with respect to the bias magnetic field, the flaws extending in various directions, which are present in the pipe P, can be detected.

Also, according to the magnetic testing apparatus 100' in accordance with this embodiment, like the magnetic testing apparatus 100 in accordance with the first embodiment, it is advantageous that a large magnetizing device for magnetically saturating the pipe P is not required and that the pipe P does not generate heat excessively even in the magnetically saturated state.

Hereunder, one example of a flaw detection test using the magnetic testing apparatus 100' in accordance with this embodiment is explained.

Example 2

In example 2 as well, as in the above-described example 1, as the pipe P, which is a test object, a carbon steel pipe containing 0.25 mass % of carbon was used. On the surface of this pipe P, an artificial axial flaw, a 15°-direction artificial flaw (an artificial flaw extending in the direction inclining at 15 degrees with respect to the pipe axis direction), a 45°-direction artificial flaw (an artificial flaw extending in the direction inclining at 45 degrees with respect to the pipe axis direction), and a 75°-direction artificial flaw (an artificial flaw extending in the direction inclining at 75 degrees with respect to the pipe axis direction) were provided. Each of the artificial flaws was made 0.5 mm in depth and 25 mm in length.

Also, in this example, as the exciting coil 112 provided in the first electromagnet 11 constituting the first rotation magnetizing device 1', a coil of 80 turns was used. The AC current supplied to the exciting coil 112 was made such that the frequency thereof was 100 Hz and the current value thereof was 10 A. Likewise, as the exciting coil 122 provided in the second electromagnet 12 constituting the first rotation magnetizing device 1', a coil of 80 turns was used. The AC current supplied to the exciting coil 122 was made such that the frequency thereof was 100 Hz and the current value thereof was 10 A. Also, as the second rotation magnetizing device 2' (tangential coil), a coil that was formed by winding the conductor 22b of 60 turns in the axial direction of the pipe P (X-direction) around the core 21, which consisted of a nonmagnetic cube one side of which was 6 mm, and by winding the conductor 22a of 60 turns in the direction substantially perpendicular to the axial direction of the pipe P (Y-direction) was used. The first AC current supplied to the conductors 22a and 22b was made such that the frequency thereof was 100 Hz and the current value thereof was 200 mA, and the second AC current supplied to the conductors 22a and 22b was made such that the frequency thereof was 20 kHz and the current value thereof was 200 mA.

Further, in this example, as the detecting device 3, a planar coil of 100 turns and 5 mm in diameter was used.

A flaw detection test was conducted under the above-described conditions.

FIGS. 7A, 7B, 7C and 7D are diagrams showing the test results of example 2. FIG. 7A shows the result of detection of the axial flaw, FIG. 7B shows the result of detection of the 15°-direction flaw, FIG. 7C shows the result of detection of the 45°-direction flaw, and FIG. 7D shows the result of detection of the 75°-direction flaw. The waveforms shown in FIG. 7 are Lissajous' waveforms prepared and displayed by the arithmetic and control device 4' based on the flaw detection signal delivered from the detecting device 3. The arithmetic and control device 4' synchronously detects the flaw detection signal with the second AC current (high frequency) supplied to the second rotation magnetizing device (tangential coil) 2' being a reference signal, and thereafter synchronously detects the flaw detection signal with the first AC current supplied to the second rotation magnetizing device (tangential coil) being a reference signal (this synchronously detected flaw detection signal is made an X signal), and also synchronously detects the flaw detection signal by delaying the phase of the reference signal (the first AC current) by 90 degrees (this synchronously detected flaw detection signal is made an Y signal). Then, the arithmetic and control device 4' vector-displays the signals on a two-dimensional plane of the X-Y coordinate system taking the X signal as an X-axis component and the Y signal as a Y-axis component. The waveform of this vector-displayed signal is the Lissajous' waveform.

It can be seen that, as shown in FIG. 7, according to the magnetic testing apparatus 100' of example 2, flaws extending in various directions, which are present in the pipe P, can be detected accurately.

REFERENCE SIGNS LIST

1 . . . first magnetizing device
1' . . . first rotation magnetizing device
2 . . . second magnetizing device
2' . . . second rotation magnetizing device
3 . . . detecting device
4, 4' . . . arithmetic and control device
20, 20' . . . flaw detecting probe
100, 100' . . . magnetic testing apparatus
F . . . flaw
P . . . pipe (test object)

The invention claimed is:

1. A magnetic testing method comprising:
   applying, to a test object, a rotating bias magnetic field which is excited by using an AC current as an exciting current;
   applying, to the test object, a rotating AC magnetic field which is excited by using a superimposed AC current in which a first AC current of the same frequency as that of the AC current that is the exciting current for the rotating bias magnetic field and a second AC current of a frequency higher than that of the first AC current are superimposed as an exciting current and which is 90 degrees out of phase with respect to the rotating bias magnetic field; and
   detecting a flaw based on leakage flux produced by the application of the magnetic fields.

2. A magnetic testing apparatus comprising:
   a first rotation magnetizing device for applying, to a test object, a rotating bias magnetic field which is excited by using an AC current as an exciting current;
   a second rotation magnetizing device for applying, to the test object, a rotating AC magnetic field which is excited by using an superimposed AC current in which a first AC current of the same frequency as that of the AC current that is the exciting current for the rotating bias magnetic field and a second AC current of a frequency higher than that of the first AC current are superimposed as an exciting current and which is 90 degrees out of phase with respect to the rotating bias magnetic field; and
   a detecting device for detecting leakage flux produced by the magnetization of the test object accomplished by the first rotation magnetizing device and the second rotation magnetizing device.

* * * * *